(12) United States Patent
Chartier-Harlin et al.

(10) Patent No.: US 6,391,553 B1
(45) Date of Patent: May 21, 2002

(54) METHOD FOR DIAGNOSING ALZHEIMER DISEASE

(75) Inventors: Marie-Christine Chartier-Harlin, Wattignies; Jean-Charles Lambert, Lille; Philippe Amouyel, Marcq en Baroeul, all of (FR)

(73) Assignees: Institut Pasteur de Lille, Lille; Institut National de la Santa et de la Recherche Medicale (Inserm), Paris, both of (FR)

( * ) Notice: Subject to any disclaimer, the term of this patent is extended or adjusted under 35 U.S.C. 154(b) by 0 days.

(21) Appl. No.: 09/446,893
(22) PCT Filed: Jun. 30, 1998
(86) PCT No.: PCT/FR98/01394
 § 371 Date: Mar. 16, 2000
 § 102(e) Date: Mar. 16, 2000
(87) PCT Pub. No.: WO99/01574
 PCT Pub. Date: Jan. 14, 1999

(30) Foreign Application Priority Data

Jul. 1, 1997 (FR) ............................................. 97 08284

(51) Int. Cl.$^7$ ............................. C12Q 1/68; C12Q 1/00; C12P 19/34; C07H 21/04
(52) U.S. Cl. ............................. 435/6; 435/4; 435/91.2; 536/24.3; 536/24.31
(58) Field of Search ................................ 435/6, 4, 91.2; 536/23.5, 24.3, 24.31

(56) References Cited

FOREIGN PATENT DOCUMENTS

WO  WO 94/09155  4/1994

OTHER PUBLICATIONS

Lambert et al., Human Molecular genetics, vol. 7(9), p. 1511–1516, Sep. 1998.*
Chartier–Harlin et al., Human Molecular Genetics, vol. 3(4), p. 569–574, 1994.*
Poirter et al., The LANCET, vol. 342, p. 697–699, Sep. 1993.*
Corder et al., Science, vol. 261, p. 921–923, Aug. 1993.*

* cited by examiner

*Primary Examiner*—Deborah J. R. Clark
*Assistant Examiner*—Shin-Lin Chen
(74) *Attorney, Agent, or Firm*—Oblon, Spivak, McClelland, Maier & Neustadt, P.C.

(57) ABSTRACT

The invention concerns a method for diagnosing Alzheimer disease, consisting in demonstrating one or several mutations in the genomic DNA region regulating the expression of the apolipoprotein E gene, inducing a modification of the apolipoprotein E gene, with respect to a control population or a modification of the expression relative to the alleles of the apolipoprotein E gene.

6 Claims, 2 Drawing Sheets

METHOD FOR DIAGNOSING ALZHEIMER DISEASE

Figure 1:
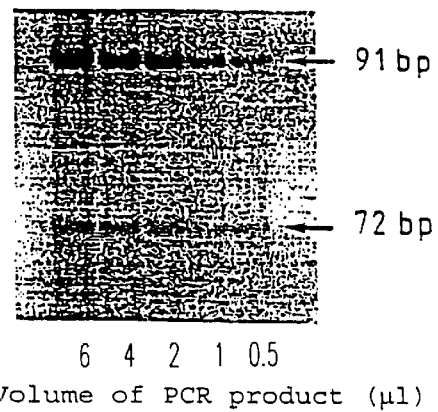

The present invention relates to a method for diagnosing Alzheimer's disease.

Alzheimer's disease is a neurodegenerative dementia characterized by a loss of cortical neurons associated with β-amyloid plaques, of neurofibrillary tangles and, in most cases, an amyloid angiopathy. It is strongly suspected that there is a genetic influence in the aetiology of Alzheimer's disease (WO 94/01772).

This genetic component has been brought to the fore over many years by indirect observations which suggest that the disease is inherited in an autosomal dominant fashion with an age-dependent penetrance in order to explain certain familial forms of Alzheimer's disease. Recent molecular genetic studies have enabled putative genes for Alzheimer's disease to be isolated by looking for chromosome-specific polymorphic genetic markers (Bird et al., 1989, Neurobiology of Aging 10, 432–434).

Four chromosomal localizations have been described as being involved: three on chromosomes 1, 14 and 21 in the early onset familial forms (age at onset under 60 years), and one on chromosome 19 in the late onset familial and sporadic forms. Two linkage studies have suggested that the chromosomal region 19q13.2 was associated with late onset familial forms of Alzheimer's disease (Pericak-Vance et al, Am. J. Hum. Genet. (1991), 48, 1034–1050). Within this chromosomal region, the group of genes for apolipoproteins (APO) E-CI-CI'-CII is a candidate zone. Among the products of these genes, apolipoprotein E (APOE) is involved especially in the nervous system APOE is present in the senile plaques and possesses a binding affinity for the peptide Aβ. APOE is characterized by three major alleles ε2, ε3, ε4. Strittmatter et al. (Proc. Natl. Acad. Sci. (1993) 90, 177–181) have described an increased frequency of the ε4 allele of the APOE gene in the late onset familial forms of Alzheimer's disease. This observation has been confirmed for the familial forms (Corder et al., Science (1993), 261, 921–923) and the sporadic forms of Alzheimer's disease (Corder et al., Science (1993), 261, 921–923; Saunders et al., Neurology (1993), 13, 1467–1472).

FR-2 716 894 describes a method which makes it possible to prognosticate, for a given disease, the risks of developing Alzheimer's disease with respect to the general population. This method is based on the detection of the ε4 alleles of the APOE gene, of the short alleles of the marker D19S178 and of the long alleles of the APO CII gene, all localized on chromosome 19.

Several hypotheses make it possible to explain this phenomenon.

Recent studies by the inventors, who are the authors of the present invention, now confirm the hypothesis of the existence of at least one other functional mutation in the 19q13.2 region.

Indeed, in addition to a functional effect specific to the polymorphism of apolipoprotein E, the studies by the inventors show differences in levels of expression which are significant in sick subjects compared with healthy controls, which indicates that one or more mutations in the regulatory regions of the APOE gene are involved in the onset of Alzheimer's disease. Furthermore, relative differences in expression are found in the controls.

The inventors have more particularly identified a new polymorphism in the region of the promoter of the gene encoding the apolipoprotein E protein found in a potential binding site for the Th1/E47cs transcription factors.

For the determination of this polymorphism, the sequence described by Paik et al. (1985, Proc. Natl. Aca. Sci., vol. 82, p. 3447) will be taken as reference.

This polymorphism has been called by the inventors Th1/E47cs for Th1/E47cs consensus, since it is situated in a consensus sequence for binding of the Th1/E47cs transcription factor.

The mutation identified is characterized by a Thymine to Guanine substitution (G→T) in the sequence:

GGGTGTCTGT(or G)ATTACTGGG,

G being the most frequent allele in the normal population.

The alleles corresponding to this polymorphism are called hereinafter T (when the base is Thymine) or G (when the base is Guanine).

The determination of the allele can be carried out after PCR amplification of the DNA region comprising this polymorphism:

- either by creating in one of the PCR primers a cleavage site for a restriction enzyme not existing in individuals carrying one of the alleles,
- or by a hybridization technique using oligonucleotide probes specific for the alleles.

The inventors have studied the influence of the Th1/E47cs polymorphism on the expression of the alleles of the APOE gene and demonstrated an increase in the risk of developing Alzheimer's disease associated with the T allele of Th1/E47cs, specific to this allele and not due to the ε4 allele.

Furthermore, the Th1/E47cs polymorphism modulates the risk associated with the ε4 allele in individuals with the ε3/ε4 genotype, the individuals with the GT genotype having an increased risk of developing Alzheimer's disease compared with the individuals homozygous for the Th1/E47cs polymorphism. Reinforcing this observation, the authors have considered that the combination of the T allele of Th1/E47cs with the ε4 allele on the same chromosome corresponds to the most unfavourable combination.

The subject of the invention is thus a method for diagnosing Alzheimer's disease, comprising the identification of one or more mutations in the genomic DNA region for regulating the expression of the apolipoprotein E gene, inducing a modification of the expression of the apolipoprotein E gene relative to a control population or a modification of the relative expression of the alleles of the apolipoprotein E gene.

For the purposes of the present invention, diagnosis is understood to mean the confirmation of a mutation in the regulatory region of the APOE gene in a patient whose clinical picture signals a symptomatology which may be attributed to Alzheimer's disease, or alternatively an increased probability in subjects of developing Alzheimer's disease relative to the population as a whole, the increase in probability being statistically significant.

The chromosomal DNA region for regulating the APOE gene is broadly defined as being the chromosomal region 19q13.2 other than the region encoding apolipoprotein E (Human Molecular Genetics, 1994, vol. 3, No. 4, 569–574).

Advantageously, the chromosomal DNA region in which one or more mutations are identified is situated between the marker D19S178 and the APOCII gene, and comprises more particularly the introns and the flanking regions of the APOE gene, extending over a distance of 5 kb upstream and downstream of the APOE gene.

The subject of the invention is more particularly a method for diagnosing Alzheimer's disease comprising the identification of at least one mutation in the promoter of the APOE gene, situated at 186 bases from the TATA box of this gene, the mutation consisting more particularly of the replacement T→G in the sequence defined above.

More particularly, the method consists in testing for one or more mutations in the region of the promoter of the gene encoding apolipoprotein E, existing in particular in a potential binding site for the Th1/E47 transcription factors.

The subject of the invention is also a method for diagnosing Alzheimer's disease comprising a determination of the genotype of apolipoprotein E and the test for a mutation of the type described above in the regulatory region of the APOE gene.

In accordance with this diagnostic method, the presence of at least one ε4 allele of apolipoprotein E conjointly with the existence of a mutation in the regulatory region of the APOE gene, in particular the mutation defined above inducing a modification of the expression of the APOE gene or a relative difference in expression of the alleles of apolipoprotein E where appropriate, will range towards the diagnosis of Alzheimer's disease in patients whose clinical picture presents a symptomatology which can be attributed to Alzheimer's disease or will make it possible to classify subjects in good health in a category with an increased risk of developing Alzheimer's disease.

Relative difference in expression of the alleles is understood to mean a difference in expression of one allele relative to another, independently of the absolute level of expression of the gene.

The test for the ε4 allele is done by any appropriate method based on the presence of an ARG residue at position 112 of apolipoprotein E for the ε4 allele, of a CYS residue at position 158 for the ε2 allele, relative to the residues CYS and ARG in these positions for the ε3 isoform, which is the most widespread.

The identification of an additional mutation in the regulatory regions of the APOE gene as defined above is carried out by any appropriate method, in particular a method for diagnosing Alzheimer's disease comprising the identification of at least one mutation in the promoter of the gene encoding APOE, situated at 186 bases from the TATA box of this gene.

The presence of at least one ε4 allele of the APOE gene, of at least one short allele of the marker D19S178 and of at least one long allele of the APO CII gene as described in FR-2,716,894 and the existence of at least one mutation in the regulatory region of the APOE gene will strongly contribute towards orienting the diagnosis of Alzheimer's disease in symptomatic subjects or will constitute a substantial risk factor in asymptomatic subjects.

Since the mutation(s) involved in Alzheimer's disease are responsible for a variation in the relative expression of the alleles of the APOE gene in the brain, it is also possible to determine, instead of or in addition to a mutation in the regulatory regions of the APOE gene which are defined above, the level of expression of the APOE gene and to compare this level of expression to that of the general population.

The diagnostic method based on the determination of the level of expression of apolipoprotein E is particularly advantageous in heterozygous subjects, in particular carrying the ε4 allele. In these subjects, the diagnostic method for the purposes of the invention advantageously comprises the determination of the level of expression of the ε4 allele relative to the ε2 or ε3 allele.

In the same manner, the diagnostic method in the individuals with the ε2/ε3 genotype advantageously comprises the determination of the level of expression of the ε2 allele relative to the ε3 allele.

An increase or a significant decrease, respectively, in the level of expression/transcription of the ε4 allele in a heterozygous subject ε4ε2 or ε4ε3 and of the ε2 allele in a heterozygous subject ε2ε3, will orient the diagnosis towards a dementia of the Alzheimer type, if moreover the subject presents a clinical picture evoking the symptomatology of Alzheimer's disease. In a subject not presenting apparent clinical signs, the increase or the decrease in expression of the ε4 and ε2 alleles, respectively, will be an indication of an increased probability in the subject of subsequently developing Alzheimer's disease.

The determination of the level of expression of the APOE gene and more particularly of the ε4 and ε2 alleles of the APOE gene is advantageously carried out by measuring the relative level of the mRNA for the APOE gene either by establishing the ratio of transcription of the ε4 allele relative to the ε2 or ε3 allele in the case of individuals with the ε4ε2 and ε4ε3 genotypes, or by establishing the ratio of transcription of the ε2 allele relative to the ε3 allele in the case of individuals with the ε2ε3 genotype.

The measurement of the level of transcription is carried out following the extraction of mRNA from biopsy tissues or from cells in cultures and amplification by RT-PCR (reverse transcription polymeric chain reaction), with the aid of appropriate primers specific for the allele for which it is desired to measure the level of expression.

The tissue used is for example derived from a biopsy of cerebral tissue, in particular of frontal lobes, thus making it possible to measure the level of expression of the alleles of APOE in the brain. It is also possible to determine the level of transcription of the mRNAs for APOE in lymphocytes or fibroblasts in cell culture. In general, it will be possible to determine the level of transcription of the alleles of APOE in any tissue capable of exhibiting a variation in the percentage of expression of an allele relative to another between the patients and those who are sick. Likewise, this method can also be applied for the development and the use of cellular or animal models using the alleles of APOE.

The ratio of the expression of the alleles of the APOE gene is determined in the following manner:

a) the cDNA is subjected to a PCR amplification in the presence of primers permitting the specific amplification of at least one polymorphic sequence of the alleles;

b) the amplified DNA is subjected to the action of at least one restriction enzyme, permitting the differentiation of the alleles;

c) the DNA fragments are separated;

d) the quantity of fragments obtained is evaluated by means of a marker emitting a detectable signal;

e) the initial ratio in the different alleles is determined by the following formula:

$$\frac{N_{oallele1}}{N_{oallele1} + N_{oallele2}} = \frac{A\alpha'_{allele1}}{A\alpha'_{allele1} + \alpha'_{allele2}}$$

in which $N_o$ is the initial number of DNA molecules,

A is the coefficient of proportionality which makes it possible to correct the size difference between the different restriction fragments and is equal to the ratio of the lengths of restriction fragments characteristic of each allele, and α' is determined either by the following formula:

$$\alpha' = \frac{OD_{max}}{K'}$$

in which $OD_{max}$ is the maximum optical density which may be measured,

K' is a constant, $OD_{max}$ and K' being determined by the following function f:

$$OD = f(V) = \frac{OD_{max}}{(K'+V)} \cdot V$$

in which V is the volume of the sample obtained by PCR subjected to step c) and OD is the optical density measured;

or by the following function g:

$$\frac{1}{QD} = g\left(\frac{1}{V}\right) = \frac{1}{\alpha'} \times \frac{1}{V} + \frac{1}{OD_{max}}$$

in which OD is the optical density measured, V is the volume of the sample obtained by PCR subjected to step c) and $OD_{max}$ is the maximum optical density which may be measured;

the coefficient of amplification $E_1$ of the DNA containing allele 1 being identical to the coefficient of amplification $E_2$ of the DNA containing allele 2, for the different alleles of APOE.

The DNA amplified in step a) is, according to the invention, a cDNA comprising the allelic sequences of interest, obtained from mRNA by the usual technique of RT-PCR. The alleles are differentiated according to steps b) and c) described above, which demonstrate the restriction polymorphisms (RFLP).

The separation of the DNA fragments according to step c) may be carried out in particular by gel electrophoresis, preferably by polyacrylamide gel electrophoresis.

In the case of the APOE gene, the ∈3, ∈2 and ∈4 alleles may be characterized by restriction fragments of 91 bp, 83 bp and 72 bp, respectively.

The coefficient of proportionality A can therefore be calculated as being A=91/72 for the ∈3/∈4 alleles, A being 83/72 for the ∈2/∈4 individuals and A being 91/83 for the ∈2/∈3 individuals. For the latter genotype, since the two ∈2 and ∈3 alleles give a restriction fragment length of 91 bp, the relationship $AOD_{allele\ 1} + OD_{allele\ 2} = OD_{91\ bp}$ is produced.

This method is in addition particularly simple. It is indeed sufficient either to present the value of the optical density (OD) as a function of the volume V of the sample, it being possible for the representative curve of the function f such that OD=f(V) to be plotted using the method of least squares, and to determine the $OD_{max}$ and K' from this curve; or to present the value 1/OD as a function of the reciprocal of the volume of the sample, that is to say 1/V, it being possible for the representative curve of the function g such that $$\frac{1}{OD} = g\left(\frac{1}{V}\right)$$

to be plotted by linear regression, the slope of the straight line obtained being equal to the reciprocal of α'.

The subject of the invention is also a method for diagnosing Alzheimer's disease comprising the determinations of the phase of the different polymorphisms ∈, and Th1/E47cs and optionally of –491 AT and 1E1 which are capable of bringing about an increased risk of developing Alzheimer's disease.

At the level of the population with the ∈3∈4 genotype, the risk associated with the GT genotype is greater than that associated with the GG genotype. This observation can be explained by taking into account the phase of the polymorphisms Th1/E47cs and ∈2, ∈ or ∈4 of APOE. Indeed, at the level of the heterozygotes GT and ∈3∈4, the risk of developing the disease depends on the combination of the G allele and of the ∈4 allele on the same chromosome, thus determining the phase of the polymorphisms ∈ and Th1/E47cs of APOE. Following this phase, two possibilities exist: (i) a higher level of expression of ∈4 (ii) a higher level of expression of the ∈3 allele. The first possibility would cause a physiological response in favour of the properties of the isomorph APO∈4 and would explain a more marked effect at the level of the individuals carrying the ∈3∈4 and GT genotypes. This difference in the level of expression linked to the phase will be true for all heterozygous genotypes. However, the risk associated with the G allele is probably attenuated because of the different combinations which are possible between the ∈ and Th1/E47cs polymorphisms of APOE.

In accordance with the invention, the phase of the polymorphisms of APOE and of Th1/E47cs is studied in the following manner:

A fragment of 4600 bp containing the ∈ polymorphisms of APOE and Th1/E47cs is amplified by PCR. This amplification is carried out using the kit: extend long template PCR system (Boehringer) with as sense oligonucleotide;

5'-GGGGGAGGTGCTGGAATCT-3' and as antisense oligonucleotide:

5'-CAGATGCGTGAAACTTGGTGA-3'.

The product of amplification is then digested with the restriction enzyme Afl III, whose sole cleavage site on the amplified fragment makes it possible to differentiate the ∈4 allele from the ∈3 allele. After migration of the product of digestion on a 0.8% agarose gel, the DNA is transferred onto nitrocellulose membrane and fixed under UV. The discrimination between the T allele and the G allele is carried out by a protocol similar to that used for the ASO genotyping of this polymorphism.

Depending on the phases of the APOE and Th1/E47cs polymorphisms, it will be possible to define subgroups of sick subjects and to determine for each subgroup the optimum therapy. Likewise, the determination of the phase with other polymorphisms of the regulatory regions of the APOE gene capable of influencing (or otherwise) its expression, such as –491 AT described by Bullido et al., 1E1, APO CI, APO CII and D19S178 could also prove useful for the determination of subgroups of subjects at high risk of developing the disease.

Thus, it is known that subjects suffering from Alzheimer's disease have a predisposition to respond to certain therapies, in particular to therapies of the cholinomimetic type depending on the type and the number of copies of the alleles of the APOE gene.

The subject of the invention is therefore also a method for identifying subjects suffering from Alzheimer's disease who are capable of responding to a given therapy, for example of the cholinomimetic type, comprising:

a) the determination of the genotype of apolipoprotein E;

b) the determination of the genotype of the Th1/E47cs polymorphism; and c) optionally, the determination of the phase of the polymorphisms of apolipoprotein E and of Th1/E47cs.

The different polymorphisms of APOE and of Th1/E47cs may be exploited to create animal or cellular models expressing APOE better or less well, used alone or in combination with the genetic factors capable of influencing the development of the pathology such as APP, PS1, PS2, and the like, or the other markers of Alzheimer's disease such as abnormal phosphorylation of the protein Tau.

The subject of the invention is therefore also a transfection vector for eukaryotic cells comprising at least one allele of the APOE gene and one allele of the Th1/E47cs polymorphism and-optionally one or more other alleles of other genes or markers close to this gene, which are capable of modifying the risk of developing Alzheimer's disease compared with a normal population.

These vectors may be used for the production of transfected eukaryotic cells or of transgenic animals.

Another subject of the invention therefore consists of the eukaryotic cells transfected by means of a vector as defined above or transgenic animals produced by means of such a vector.

The results of a study of the levels of expression of the mRNAs for the APOE gene in the brain will be given below.

EXAMPLE 1

Expression, in the Brain, of the APOE Gene in Patients Suffering from Alzheimer's Disease Compared with Healthy Controls 1) Extraction of the RNA and amplification of the transcripts The tissues were chosen in controls aged 65 years or over and in patients suffering from late onset Alzheimer's disease, whose diagnosis has been confirmed by neuropathological examination, with heterozygous APOE genotypes.

The extraction of the RNA was carried out on samples of frontal lobes as described in J. Biol. Chem. 247, 4621–4627 (1972), or using an extraction kit (QIAGEN) and then the RNA was digested with DNase (Eurogentec). The RT-PCR was carried out with the aid of the primers described in J. Lipid. res. 31, 545–548 (1990). The reverse transcription reaction was carried out for 1 h 30 min at 37° C., with the aid of primer F4 (5'-ACAGAATTCGCCCCGGCCTGGTA-3') at 50 pmolar with 1 μg of total RNA as template for the M-MLV reverse transcriptase, in accordance with the manufacturer's instructions (Gibco/BRL). The PCR was carried out at 94° C. for 10 minutes, followed by 30 cycles at 58° C. for 1 minute, 72° C. for 1 minute and 94° C. for 1 minute.

The reaction volume of 25 μl for the PCR contained the primer F6 (5'-TAA GCT TGC CAC GGC TGT CCA AGG A-3') at 50 pmolar, the dNTPs at 0.5 mM, $MgCl_2$ at 0.1 mM, triton X-100 at 0.1%, glycerol at 15% and Taq-Polymerase at 0.05 units (Eugentec).

The method of calculating the differential expression of the mRNAs is that described above.

The OD was estimated by the software ®Imagemaster (Pharmacia).

The length of restriction fragments was determined at 91 bp for the allele ε3, 83 bp for the allele ε2 and 72 bp for the allele ε4.

The value of the coefficient A corresponds for the genotypes ε3ε4 and ε2ε4 to A=91/72 and A=83/72 respectively. The value of the coefficient A corresponds for the genotypes ε2ε3 to A=91/83. The genotype ε2ε3 is characterized by the bands at 94 and 83 bp. In this case, given that the two alleles ε2 and ε3 give restriction fragments of 91 bp, AODε2=ODε3=OD 91 bp.

2) Results

Figure 2:
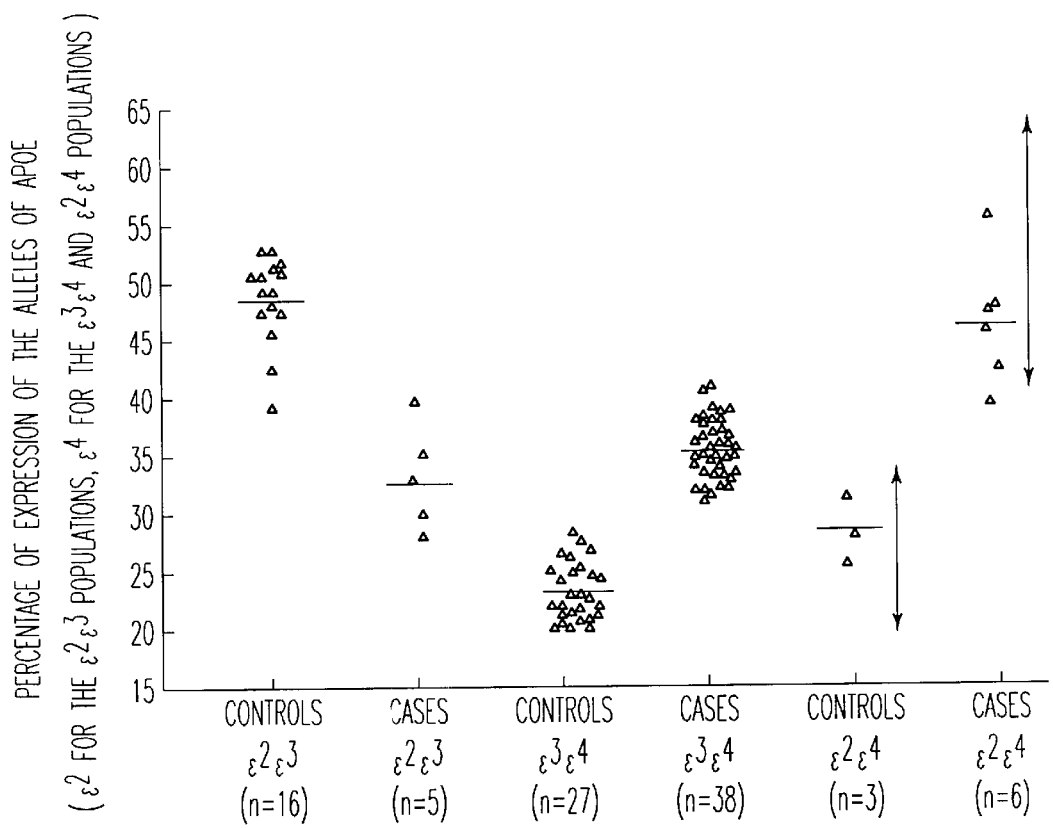

The results are presented in FIGS. 1 to 4:

FIG. 1 representing the products of amplification by RT-PCR after staining;

FIG. 2 representing the expression of the mRNAs of heterozygous individuals ε2ε3, ε3ε4 and ε2ε4 suffering from Alzheimer's disease and of controls. The black lines represent the mean values. The arrows represent the expected values of the level of expression of the ε4 allele in the individuals with the ε2/ε4 genotype. These values were estimated from the percentages observed for the alleles ε2 and ε4 in the individuals with the ε2/ε4 and ε3/ε4 genotypes, respectively.

Figure 3:
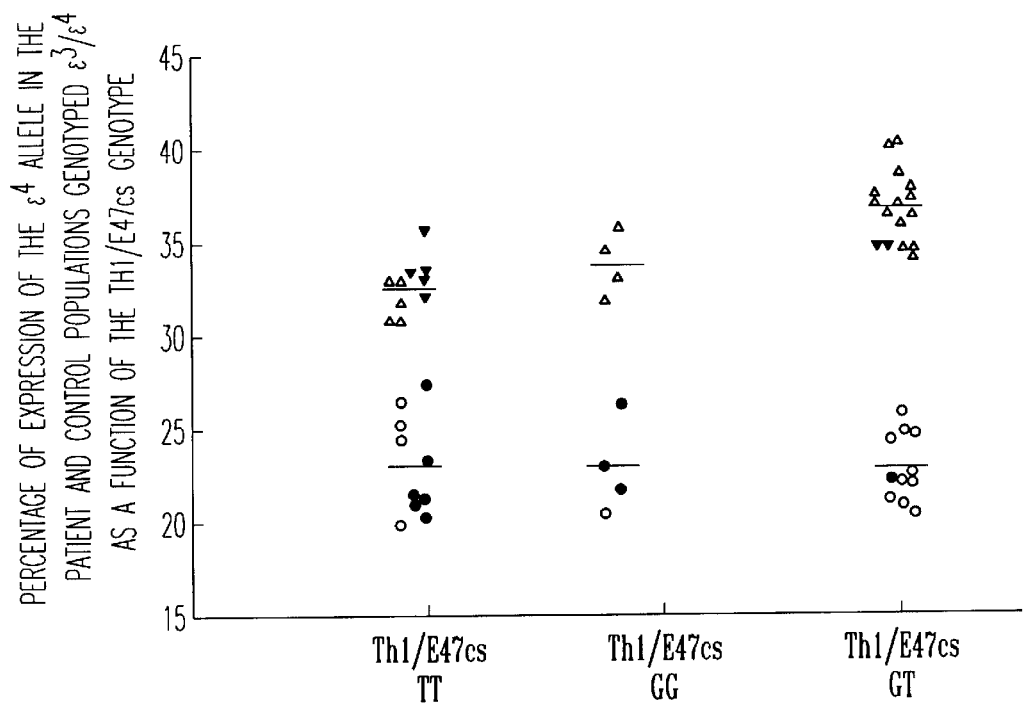

FIG. 3 represents the measurement of the level of expression of the allele ε4 in young healthy subjects presenting no cognitive disorders at the time of sampling and in demented subjects presenting a probable diagnosis of Alzheimer's disease.

Figure 4:
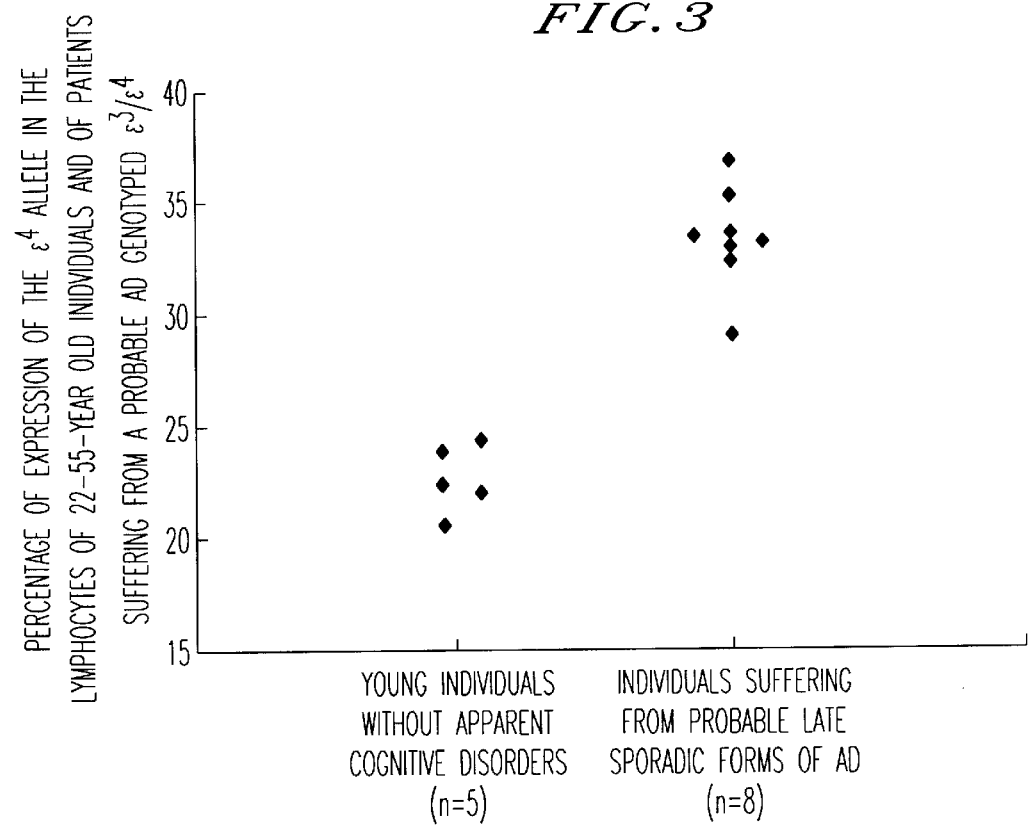

FIG. 4 represents the percentage of expression of the ε4 allele in the patients and controls as a function of the Th1/E47cs and −491 AT genotypes. The control individuals are represented by the circles and the sick individuals by the triangles. The black motifs correspond to the individuals genotyped heterozygous for the −491 AT polymorphism. The mean values for expression are represented by the black bars.

The number of subjects was 49 for the patients suffering from Alzheimer's disease and 45 for the controls.

The results show that the expression of the mRNA for the ε3 allele was, in all cases, higher than that of the mRNA for the ε4 allele, this in all the individual cases. This result is consistent with the known measurements of the levels of the APOE proteins found in the brains of individuals whose genotype has been determined. In this study, it has been shown that the level of APOE in the ε3 homozygotes was higher than that for the ε3ε4 heterozygotes which was itself higher than that for the ε4 homozygotes. Added to each other, the results may suggest either that there is a difference in stability of the different mRNA species or that there is a genetic variability in the expression of the two alleles in disequilibrium with the genetic polymorphism. However, given that a clear and consistent difference further exists in the ratio of allelic expression between the patients and the controls, the second hypothesis is probably the correct one. The patients suffering from Alzheimer's disease present a higher relative expression of ε4 mRNA than the controls (34.9±2.7% against 22.9±2.4 respectively; p<0.0001 by a Mann and Whitney nonparametric test) (FIG. 1). An increase in expression of the ε4 allele is also detected in the patients with the ε2ε4 genotype compared with the controls of the same genotype (46.0±5.4% against 28.0±2.8%, p<0.01). On the other hand, a significant decrease in the relative expression of the ε2 allele is demonstrated in the brain of the patients with the ε2ε3 genotype compared with the controls of the same genotype (32.8±4.5% against 47.8±3.9%, p<0.002) (FIG. 1). Confirming the data obtained, the values measured in the sick or control individuals with the ε2ε4 genotype correspond to the values estimated from the other genotypes (FIG. 1).

With the aim of knowing if the difference of expression of the alleles of APOE is specific to the brain or can be found in other tissues which are easier to obtain from the living patient (lymphocytes, fibroblasts and the like), the authors have studied the diffential expression of the alleles of APOE in the lymphocytes. The results relating to this study will be given below.

EXAMPLE 2

Expression, in the Lymphocytes, of the APOE Gene in Individuals Suffering from Alzheimer's Disease and Young Individuals Presenting, at the Time of the Study, no Cognitive Disorders 1) Separation of the lymphocytes and culture A blood sample is collected from individuals probably having Alzheimer's disease and from young individuals having no cognitive disorders at the time of the study. All these individuals have the specific feature of having the ε3ε4 genotype.

The separation of the lymphocytes was carried out on Leucosep tube containing a Ficoll gradient. After several washings of the lymphocytes with RPMI, they are resuspended in a culture medium composed of RPMI, 10% FCS, 2 mM glutamate, 100 μM streptopenicillin and 1% of phytohaemaglutinin (Gibco/Brl). The cell concentration is then 1 million cells per ml. The cells in suspension are cultured for 48 hours for example.

2) Extraction of the RNA and amplification of the transcripts

The methods used are those described above in Example 1.

3) Results

The authors observe a higher level of expression of the ε3 allele compared with the ε4 allele in all the individuals studied (whether they are sick or controls), thus corresponding to the observations made in the cerebral tissue. In the lymphocytes, the patients express the ε4 allele at a level close to that observed at the level of the brains of patients with the ε3ε4 genotype. Out of the 7 potentially sick individuals, all exhibit a level of expression of the ε4 allele similar to that obtained from cerebral samples from individuals for whom the diagnosis of Alzheimer's disease is certain.

The authors studied the relative expression of the ε4 allele in 5 individuals with the ε3ε4 genotype and aged 23 to 55 years and having no cognitive disorders at the time of sampling. This is intended to determine if a modification of the level of expression of the ε4 allele can be visible in individuals presenting no clinical sign of Alzheimer's disease. There could therefore be a possibility of determining early the individuals at greater risk of developing Alzheimer's disease. Of the 5 individuals studied, all exhibited a level of expression close to that observed in the brain of the controls. These results suggest that the sensitivity and the specificity of this test is therefore excellent.

In conclusion, it is advantageous to note that the relative level of expression of the ε4 allele could be similar in the cerebral tissue of definite Alzheimer-type patients and the lymphocytes of probable Alzheimer-type patients. Likewise, this level of expression could be similar in these two cell types for people presenting no cognitive disorders. Up until now, all the hypotheses seeking to implicate the role of APOE in Alzheimer's disease were based on the fact that the different alleles of APOE were expressed in an equivalent manner and at identical concentrations in the brain. The results of the present invention show for the first time that this is not the case and that the alleles are expressed differently and that this difference is significantly more marked in patients suffering from Alzheimer's disease compared with the control population. The same type of study for the other heterozygous genotypes of the APOE gene as well as an absolute quantification of the APOE gene regardless of the genotype is in progress.

In conclusion, the results obtained up until now are on agreement with the existence of a mutation in the regulatory regions of the APOE gene.

The results which led to the demonstration of the Th1/E47cs polymorphism will be given below.

EXAMPLE 3

Characterization of the Th1/E47cs Polymorphism and its Impact in Alzheimer's Disease.

1. Sequencing of APOE

A fragment of 375 base pairs was amplified by PCR with the primers for the sense strand 5'TACTTTCTTTCTGG-GATCCAGG 3' and for the antisense strand 5'ACTCAAG-GATCCCAGACTTG 3'. The amplification is carried out over 35 cycles (temperature for hybridization of the oligonucleotides: 53° C.) in a buffer containing 1 mM MgCl$_2$ final. The fragment obtained was sequenced according to the conditions described in the kits for pretreatment (US 70993-Amersham) and sequenceing (USB-Amersham-T7 PCR product sequencing kit).

2. Detection of the polymorphism poly LBP1 by restriction enzyme

The amplification of a fragment of 228 base pairs containing the poly LBP1 polymorphism was carried out over 40 cycles in the presence of 0.5 mM MgCl$_2$, 0.5% DMSO. The temperature for hybridization of the oligonucleotides is 53° C. The antisense oligonucleotide is identical to that used for the sequencing. The sense oligonucleotide is the following: 5'AGAATGGAGGAGGGTGCCTG 3'. The modified nucleotide permitting the creation of a cleavage site with the G allele for the restriction enzyme Bstn I is represented in bold. The digestion is carried out at 60° C. overnight. The products of digestion are separated on a 12% polyacrylamide gel (acrylamide:bisacrylamide 19:1) and stained in an ethidium bromide bath. The T allele is characterized by a restriction fragment at 49 bp and the G allele by a restriction fragment at 31 bp.

3. Detection of the polymorphism by annealing of oligonucleotides specific for each allele (Annealing Specific Oligonucleotide or ASO)

The ASO technique used to detect the poly LBP1 polymorphism is based on the protocol described by Tiret et al., (1994, Lancet, vol. 344, 910–913). The modifications specific to the detection of the poly LBP1 polymorphism relating to the oligonucleotides and the washing temperatures are the following: oligonucleotide specific for the G allele has the sequence 5'GCCCAGTAATCCAGACACCC 3' with a washing temperature 61° C., the oligonucleotide specific for the T allele has the sequence: 5'GCCCAG-TAATACAGACACCC 3' with the washing temperature 62° C.

4. Results

The first European population used in this study comprises 310 controls (age=73.5±10.9; 37.3% men) and 293 subjects suffering from early and late sporadic forms of Alzheimer's disease (age=74.6±9.3; age at the start of the disease=71.0±8.9; 32.2% men). Three polymorphisms of the locus of APOE were tested on this population: the Th1/E47cs polymorphism using the methods described above, the 1E1 polymorphism according to the technique used by Mui et al., (Neurology, 1996, vol. 47, 196–201), the polymorphism of APOE according to the technique of Hixon and Vernier (J. Lipid. Res. vol. 31, 545–548). The number of subjects varies according to the polymorphism studied: study of Th1/E47cs, 279 sick individuals and 310 controls; study of 1E1, 293 sick individuals and 307 controls.

In order to improve the statistical power of the study for the analyses at the level of the individuals heterozygous for the APOE genotype, the authors increased the number of individuals of ε3/ε4 genotype-by adding subjects of this genotype from independent populations so as to finally obtain a total of 152 sick individuals and 91 controls (respectively 73.3±8.5 and 70.3±8.5 years).

The distribution of the three polymorphisms studied is presented in Table 1. No deviation relative to the Hardy-Weinberg equilibrium was observed for each of these polymorphisms.

The tendency to develop the disease is expressed by a factor for approximating the relative risk OR (for "Odd Ratio").

CI represents the confidence interval at 95%.

The results are presented in Tables 1 to 5.

As expected, the ε4 allele is closely associated with Alzheimer's disease (OR=4.67 CI 95% [3.28–6.67]), whereas the ε2 allele shows a protective effect (OR=0.27 CI 95% [0.14–0.52]). In the control population, the G allele of Th1/E47cs is the most represented (0.531) contrary to what is observed in the sick population (0.468). The allelic and genotype distributions are significantly different in the sick individuals compared with the controls (respectively p=0.03 and p=0.007). The T allele of Th1/E47cs is associated with an increased risk of developing Alzheimer's disease (OR= 1.29 CI 95% [1.02–1.63]) and the OR is 1.79 (CI 95% [1.21–12.65], p=0.002) for the individuals carrying at least one T allele. For the 1E1 polymorphism, the allelic and genotype distributions are significantly different between the two populations (respectively p=0.002 and p=0.0005). The C allele of 1E1 is associated with a decrease in the risk of developing the pathology (OR=0.56 CI 95% [0.40–0.78], p=0.0003).

The authors calculated the linkage disequilibrium, in pairs, for the different polymorphisms studied (Table 2). A significant linkage disequilibrium exists between the Th1/E47cs, 1E1 and APOE polymorphisms. The authors then estimated the haplotypes generated by these three polymorphisms using the Myriad Haplotype algorithm (Table 3). The estimated distribution of the haplotypes is significantly different between the population of sick individuals and that of the controls. Moreover, in order to take into account the strong association of the ε4 allele with Alzheimer's disease, the authors compared the estimated distribution of the haplotypes in the subgroups of ε3/ε3 and ε3/ε4 genotype, this distributions being significantly different between the patients and the controls (Table 3). These results suggest that the Th1/E47cs and 1E1 polymorphisms have a specific effect compared with the ε polymorphisms of APOE.

In the general population (patients=261 and controls= 253), the authors estimated the risk of developing Alzheimer's disease for individuals possessing at least one allele of each of the polymorphisms, this estimation being made in the first instance independently between these polymorphisms. A significant effect is then observed for the polymorphisms (Table 4). When all the polymorphisms are taken into account simultaneously in a logistic regression, the effects of Th1/E47 and 1E1 persist and even increase, supporting the hypothesis that several polymorphisms might exist inside the locus of APOE.

If the level of expression of the alleles of APOE is increased by the existence of mutations in cis in the promoter region of the APOE gene, three implications should be verified: (1) the mutation situated in the promoter should modulate the expression of the alleles of APOE, thus revealing the deleterious effect of the ε4 allele or accentuating the protective effect of the ε2 allele; (2) given that what determines the risk would be the relative level of expression of the two alleles of APOE in the heterozygous individuals, this mutation should not have the same impact in the population of genotype heterozygous for APOE compared with the population of homozygous genotype. (3) the effect of a mutation in cis in the heterozygous individuals should depend on the phase of this polymorphism with the alleles of APOE, (i.e. the haplotype). In the individuals carrying a copy of the ε4 allele heterozygous for the genotype of Th1/E47cs, the ε4 allele may be associated either with the T allele, or with the G allele of Th1/E47cs. One of these combinations ought to increase the relative level of expression of the ε4 allele and to decrease that of the ε3 allele, the other combination then having the opposite effect.

Thus, in the individuals of ε3/ε4 genotype, the risk of developing Alzheimer's disease will be different between the individuals heterozygous and homozygous for Th1/E47cs. To test these hypotheses, the authors studied the risk of developing the pathology (adjusted on the sex and the age) of the individuals heterozygous for Th1/E47cs compared with the individuals homozygous for this same polymorphism. Only the individuals heterozygous for the Th1/E47cs genotype and for that of APOE exhibit an increase in the risk of developing the pathology (OR=2.40 CI 95% [1.40–4.12], p=0.001), this effect not being found for the individuals homozygous for the APOE genotype (OR=1.02 CI 95% [0.67–1.57], p=0.91). This impact is demonstrated in particular in the subpopulation of ε3/ε4 genotype since the risk of developing Alzheimer's disease for the individuals heterozygous for the Th1/E47cs genotype is increased compared with the individuals homozygoug for this genotype (OR=1.90 CI 95% [0.97–3.70], p=0.06; patients=107 and controls=54). This increase in the risk becomes significant by extending the population of ε3/ε4 genotype (OR=2.07 CI 95% [1.21–3.54], p=0.008; patients=152 and controls=91) (Table 5). By using a step by step logistic regression, the authors have shown that the risk of developing the pathology is modified only in the individuals heterozygous for the Th1/E47cs genotype (OR=1.89, εI 95% [1.07–3.35], p=0.027) and not in the individuals heterozygous for the 1E1 genotype. These results therefore suggest that between the two polymorphisms Th1/E47cs and 1E1, Th1/E47cs would be a better candidate for modifying the relative level of expression of the alleles of APOE.

In order to apprehend the influence of the phase of the Th1/E47cs and APCE polymorphisms on the risk of developing Alzheimer's disease, the authors estimated the frequencies of the haplotypes corresponding to association of the T or G alleles of Th1/E47cs with the ε4 allele in the individuals of the ε3/ε4 genotype either for the patients or the controls. For the individuals carrying the ε3/ε4 and GT genotypes, 57.6% of the controls are thought to exhibit the association of the T and ε4 alleles on the same chromosome, this proportion passing to 69.7% in the patients. The estimated OR is then 1.7 for the individuals exhibiting this haplotype, a result which again suggests that the Th1/E47cs polymorphism is capable of influencing the level of expression of the ε4 allele.

To confirm these results, the authors studied the impact of the Th1/E47cs polymorphism in a larger population of cases and controls. Furthermore, they combined with this study a new polymorphism in the promoter of the gene for APOE, −491 AT (Bullido et al., Nat. Genet, 1998), which is also capable of modifying the level of expression of APOE. The selected population comprises 573 sporadic cases probably having Alzheimer's disease (age=73.8±8.1 years, age at the start of the disease=70.4±7.9 years, 35.9% men) and 509 controls (age=74.9±9.9 years, 35.9% men).

As above, this population is adapted in order to study the impact of the APOE gene in Alzheimer's disease, since the ε4 allele is strongly associated with the pathology (OR=5.40 CI 95% [4.11–7.09], p<0.0001) whereas the ε2 allele exhibits a protective effect (OR=0.47 CI 95% [0.31–0.70], p=0.0003). The frequency of the T allele of the Th1/E47cs polymorphism in increased in the cases compared with the controls (Table 6) and the risk of developing AD for the individuals carrying at least one T allele is 2.13 (CI 95% [1.61–2.83]).

At the level of the study of the −491 AT polymorphism, first of all the authors observed a similar distribution of the allelic and genotype frequencies to those described above in the North American population. The frequency of the T allele of the −491 AT polymorphism is reduced in the patients compared with that of the controls and the OR associated with the risk of developing AD for the individuals carrying at least one T allele of the −491 AT polymorphism is 0.67 (CI 95% [0.52–0.88], p=0.004) (Table 4).

In order to eliminate a possible bias due to the ε4 allele on the association of the two Th1/E47cs and −491 AT polymorphisms with AD, the authors tested the effects of each allele using a logistic regression adjusted on the presence or the absence of the ε4 allele. After adjustment, the risk associated with the presence of at least one T allele of the Th1/E47cs polymorphism persists (OR=1.56 CI 95% [1.15–2.11], p=0.004), whereas the risk associated with the presence of at least one T allele of the −491 AT polymorphism disappears (OR=0.82 CI 95% [0.62–1.10], p=0.19). This observation suggests that the effect of the T allele of Th1/E47cs is not explained by the presence of the ε4 allele. As suggested above during the first study, if it is assumed that the level of expression of the alleles of APOE is increased or decreased as a function of cis mutations in the region of the promoter, these mutations should have a different and detectable effect mainly in the ε2/ε3/ε4 heterozygous individuals. In order to verify this hypothesis, the ORs associated with the risk of developing AD were studied in the individuals heterozygous and homozygous for the APOE genotype using a logistic regression adjusted on age, sex and the presence of at least one T allele of the Th1/E47cs and −491 AT polymorphisms. In the ε2/ε3/ε4 homozygous individuals, no effect is detected (OR=1.13, CI 95% [0.77–1.65] and OR=0.99 CI 95% [0.68–1.44] for the individuals carrying at least one T allele of Th1/E47cs and −491 AT, respectively). On the other hand, in the ε2/ε2/ε4 heterozygous individuals, those who possess at least one T allele of Th1/E47cs exhibit an increase in the risk of developing the pathology (OR=3.57 CI 95% [2.22–5.75], p<0.0001), contrary to those carrying at least one T allele of −491 AT who exhibit a protective effect (OR=0.57 CI 95% [0.37–0.90], p=0.014]). These observations are therefore in agreement with the authors' initial hypotheses.

Thus, the authors' results, obtained by two epidemiological studies, show that the promoter region of the APOE gene possess mutations capable of promoting the development of Alzheimer's disease, in particular the Th1/E47cs polymorphism, independently of the polymorphisms of the APOE gene. This polymorphism modifies the impact of the ε4 allele in the population studied, defining within the ε3/ε4 population, subpopulations presenting different risks, the individuals being heterozygous for the Th1/E47cs polymorphism presenting the highest risk. The estimation of the phase makes it possible to better understand the subpopulation most at risk, that is to say that exhibiting the combination of the ε4 allele and of the T allele on the same chromosome.

The influence of these polymorphisms can be explained by an increase in the level of expression of the ε4 allele or a decrease in the expression of the ε2 allele relative to the other alleles, this hypothesis being supported by the analysis of the differential expression of the mRNAs derived from the alleles of APOE in the brain of the patients and of the controls.

It will be important to study the phase between these two polymorphisms using alleles specific for each of the polymorphisms.

Thus, in a first instance, by two epidemiological studies, the authors have demonstrated the specific effects of two polymorphisms on the risk of developing AD, the T allele of Th1/E47cs and of −491 AT having respectively a deleterious and protective effect. In a second instance, the authors observed a marked differential expression of the alleles of APOE, the ε4 allele being overexpressed in the patients of ε3ε4 and ε2ε4 genotype, and the ε2 allele being underexpressed in the ε2ε3 patients compared with the controls of the same genotype. Finally, in agreement with the data deduced from the studies of the control cases, the level of expression of the ε4 allele in the brain of the ε3ε4 patients is correlated with the mutations present in the regulatory region of the APOE gene. The T allele of Th1/E47cs increases the relative level of expression of the ε4 allele in the patients, whereas the T allele of −491 AT decreases it (FIG. 3 and Table 5). These results are in agreement with recent data, suggesting a modification of the expression of the APOE gene by these two mutations in a hepatoma cell line.

It is important to note that the Th1/E47cs polymorphism is localized in a consensus site for binding of the transcription factor Th1/E47 and more particularly in the site for binding of the helix-loop-helix transcription factor E47. This factor belongs to the class A proteins which are expressed ubiquitously and form multiple combinations with the class B proteins for controlling the tissue-specific expression of genes (Murre et al., Cell. Vol. 15, 451–459). In particular, E47 is expressed in the brain, combined with multiple class B proteins and involved in the development and maintenance of the nervous system in mammals. On the other hand, little is known about the transcription factor Th1, identified during a screening of mouse embryo cDNA library. A homologous protein had been described in drosophila, combined with the class A transcription factor, Daughterless, whose expression is essential in neurogenesis.

In conclusion, all the data gathered by the authors suggest that the study of the expression of the APOE gene would make it possible to carry out a diagnosis in individuals heterozygous for the APOE genotype, but also to better define subpopulations at risk. This information will therefore be important for defining new therapeutic targets and for prescribing the optimum treatments.

TABLE 1

Combination of the different alleles of the APOE Th1/E47cs and 1E1 polymorphisms in the control and patient populations.

| | | Allelic frequency | | | Genotypic frequency | | | | | |
|---|---|---|---|---|---|---|---|---|---|---|
| APOE | N | ε2 | ε3 | ε4 | ε2/ε2 | ε2/ε3 | ε2/ε4 | ε3/ε3 | ε3/ε4 | ε4/ε4 |
| Controls | 308 | 0.081 | 0.805 | 0.114 | 0.003 | 0.133 | 0.230 | 0.649 | 0.179 | 0.130 |
| Patients | 292 | 0.034 | 0.639 | 0.327 | — | 0.034 | 0.034 | 0.425 | 0.393 | 0.113 |
| Th1/E47cs | N | G[a] | T | | GG[b] | GT | TT | | | |
| Controls | 310 | 0.531 | 0.469 | | 0.320 | 0.422 | 0.258 | | | |
| Patients | 279 | 0.468 | 0.532 | | 0.208 | 0.520 | 0.272 | | | |
| 1E1 | n | G[c] | C | | GG[d] | GC | CC | | | |
| Controls | 307 | 0.615 | 0.385 | | 0.388 | 0.456 | 0.156 | | | |
| Patients | 293 | 0.711 | 0.289 | | 0.533 | 0.382 | 0.085 | | | |

| | N | ε2/ε3* | ε3/ε3 | ε3/ε4 | ε4/ε4 | ε2/ε4 |
|---|---|---|---|---|---|---|
| Combination of the APOE and 1E1 polymorphisms | | | | | | |
| Patients | | | | | | |
| CC | 22 | 1 | 20 | — | 1 | — |
| GC | 100 | 4 | 50 | 46 | — | — |
| GG | 139 | 4 | 44 | 56 | 27 | 8 |
| n | 261 | 9 | 114 | 102 | 28 | 8 |
| Controls | | | | | | |
| CC | 41 | 0 | 41 | 0 | — | — |
| GC | 112 | 12 | 76 | 24 | — | — |
| GG | 100 | 25 | 50 | 15 | 3 | 7 |
| n | 253 | 37 | 167 | 39 | 3 | 7 |
| Combination of APOE and Th1/E47cs polymorphisms | | | | | | |
| Patients | | | | | | |
| GG | 55 | 4 | 36 | 13 | 1 | 1 |
| GT | 134 | 5 | 54 | 60 | 8 | 7 |
| TT | 78 | — | 24 | 29 | 19 | — |
| n | 261 | 9 | 114 | 102 | 28 | 8 |
| Controls | | | | | | |
| GG | 85 | 25 | 52 | 5 | — | 3 |
| GT | 108 | 11 | 76 | 16 | 1 | 4 |
| TT | 60 | 1 | 39 | 18 | 2 | — |
| n | 253 | 36 | 167 | 39 | 3 | 7 |

[a] $p < 0.001$:
[b] $p = 0.03$. OR (T**/T*) = 1.29 CI 95% [1.02–1.63]:
[c] $p = 0.007$:
[d] $p = 0.002$. OR (G**/G*) = 1.44 CI 95% [1.14–1.84]:
[e] $p = 0.0005$:
[f] NS: one individual is genotyped ε2/ε2 in the control population.

TABLE 2

Disequilibrium of the linkage in the chromosomal region 19q13.2 region.

| | Th1/E47cs | 1E1 | APOE |
|---|---|---|---|
| Cases | | | |
| Th1/E47cs | — | −8.4 | −5.8 |
| 1E1 | 79 | — | −6.1 |
| APOE | 49 | 54 | — |
| Controls | | | |
| Th1/E47cs | — | 11.9 | −1.9 |
| 1E1 | 86 | — | −3.7 |
| APOE | 32 | 42 | — |

The APOE polymorphism was analysed as a biallelic marker (i.e. allele 4 versus allele 2 or 3)

The standardized coefficient Δ of linkage disequilibrium is represented above the diagonal of the table. The maximum percentage D' of the linkage disequilibibrium for the given allelic frequencies is represented below this diagonal.

TABLE 3

Estimation of the possible haplotypes between the different polymorphisms studied in the chromosomal region 19q.13.2. The anonymous marker D19S178 was integrated into this study.

| | Polymorphisms | | | | Estimated frequencies of haplotypes | | |
|---|---|---|---|---|---|---|---|
| Haplotype Number | D19S178 | Th1/E47cs | 1E1 | APOE | Cases | Controls | Controls expected | a. General population

| | | | | | | | |
|---|---|---|---|---|---|---|---|
| 1  | S | T | G | ε4⁻ | 0.130 | 0.032 | 0.029 |
| 2  | S | T | C | ε4⁻ | 0.004 | 0.000 | 0.019* |
| 3  | S | G | G | ε4⁻ | 0.031 | 0.006 | 0.035* |
| 4  | L | T | G | ε4⁻ | 0.100 | 0.043 | 0.027 |
| 5  | L | T | C | ε4⁻ | 0.005 | 0.000 | 0.018* |
| 6  | L | G | G | ε4⁻ | 0.044 | 0.022 | 0.033 |
| 7  | L | G | C | ε4⁻ | 0.003 | 0.000 | 0.021* |
| 8  | S | T | G | ε4⁻ | 0.018 | 0.009 | 0.114* |
| 9  | S | T | C | ε4⁻ | 0.127 | 0.183 | 0.072* |
| 10 | S | G | G | ε4⁻ | 0.184 | 0.267 | 0.142* |
| 11 | S | G | C | ε4⁻ | 0.000 | 0.011 | 0.087* |
| 12 | L | T | G | ε4⁻ | 0.020 | 0.014 | 0.113* |
| 13 | L | T | C | ε4⁻ | 0.128 | 0.170 | 0.070* |
| 14 | L | G | G | ε4⁻ | 0.195 | 0.224 | 0.136* |
| 15 | L | G | C | ε4⁻ | 0.011 | 0.019 | 0.084* |
| Number of chromosomes | | | | ε4⁻ | 522 | 506 | |
| | | | | ε4⁻ | | | | b. Population ε3/E3 genotype

| | | | | | | | |
|---|---|---|---|---|---|---|---|
| 1 | S | T | G | | 0.035 | 0.014 | 0.129* |
| 2 | S | T | C | | 0.192 | 0.239 | 0.116* |
| 3 | S | G | G | | 0.259 | 0.268 | 0.151* |
| 4 | S | G | C | | 0.009 | 0.013 | 0.136* |
| 5 | L | T | G | | 0.027 | 0.010 | 0.113* |
| 6 | L | T | C | | 0.193 | 0.198 | 0.103* |
| 7 | L | G | G | | 0.285 | 0.234 | 0.133* |
| 8 | L | G | C | | 0.000 | 0.024 | 0.119* |
| Number of chromosomes | | | | | 228 | 334 | | c. Population ε3/ε4 genotype

| | | | | | | | |
|---|---|---|---|---|---|---|---|
| 1 | S | T | G | | 0.184 | 0.154 | 0.207 |
| 2 | S | T | C | | 0.102 | 0.148 | 0.092 |
| 3 | S | G | G | | 0.169 | 0.145 | 0.103 |
| 4 | s | G | C | | 0.000 | 0.000 | 0.046 |
| 5 | L | T | G | | 0.179 | 0.204 | 0.254 |
| 6 | L | T | C | | 0.113 | 0.158 | 0.127 |
| 7 | L | G | G | | 0.237 | 0.188 | 0.113 |
| 8 | L | G | C | | 0.015 | 0.000 | 0.056 |
| Number of chromosomes | | | | | 204 | 78 | |

TABLE 4

ORs estimated by multiple logistic regression

| OR 95% CI | Th1/E47cs TT + GT/GG | 1E1 CC + GC/GG | APOE with ε4/without ε4 |
|---|---|---|---|
| Non adjusted | 1.79 [1.21–2.65] P = 0.002 | 0.56 [0.40–0.78] p = 0.0003 | 4.32 [2.98–6.28] p < 0.0001 |
| Adjusted on the sex and age | 1.90 [1.28–2.83] P = 0.002 | 0.58 [0.41–0.82] p = 0.002 | 4.66 [3.14–6.93] p < 0.0001 |
| Adjusted on the sex, age and other polymorphisms | 2.51 [1.38–4.56] P = 0.001 | 0.43 [0.25–0.74] p = 0.002 | 3.22 [2.06–5.02] p < 0.0001 |

TABLE 5

Distributions of the 1E1 and Th1/E47cs genotypes in the extended ε3ε4 population.

| | | 1E1 polymorphism[a] | | Th1/E47cs polymorphism[b] | | |
|---|---|---|---|---|---|---|
| | N | GG | GC | GG | GT | TT |
| Controls | 91 | 50 | 41 | 16 | 38 | 37 |
| Cases | 152 | 67 | 85 | 19 | 89 | 44 |

[a] = 0.10;
[b] = 0.04.

TABLE 6

Allelic and genotypic distribution of the APOE Th1/E47cs and -491 AT polymorphisms.

| APOE | Allele | | | Genotype | | | | | |
|---|---|---|---|---|---|---|---|---|---|
| | ε2 | ε3 | ε4 | ε2ε2* | ε2ε3 | ε2ε4 | ε3ε3 | ε3ε4 | ε4ε4 |
| Controls | 75(0. | 832(0 | 111(0 | 4(0.0 | 57(0. | 10(0. | 344(0 | 88(0. | 6(0.0 |
| Cases | 40(0. | 699(0 | 407(0 | — | 16(0. | 24(0. | 223(0 | 237(0 | 73(0. |
| Th1/E47cs | G | T | | GG* | GT | TT | | | |
| Controls | 562(0 | 456(0 | | 162(0 | 238(0 | 109(0 | | | |
| Cases | 515(0 | 631(0 | | 103(0 | 308(0 | 162(0 | | | |
| -491 AT | A | T | | AA† | AT. | TT | | | |
| Controls | 833(0 | 185(0 | | 343(0 | 147(0 | 19(0. | | | |
| Cases | 993(0 | 153(0 | | 432(0 | 129(0 | 12(0. | | | |

The number of alleles (frequency) is presented.
The genotypic distributions are in Hardy-Weinberg equilibrium in the control populations.
*$p < 10^{-4}$; †$p = 0.005$.

TABLE 7

Relative expression of the ε4 allele in the patients and the controls as a function of the Th1/E47cs and -491 AT polymorphisms.

| | n | Cases | n | Controls* |
|---|---|---|---|---|
| Th1/E47cs | | | | |
| GG | 4 | 33.5 ± 1.7% | 4 | 22.5 ± 2.5% |
| GT | 19 | 36.3 ± 2.1% | 11 | 22.6 ± 1.9% |
| TT | 10 | 32.4 ± 1.4% | 10 | 22.8 ± 2.7% |
| -491 AT | | | | |
| AA | 26 | 35.3 ± 2.7% | 15 | 22.8 ± 2.2% |
| AT | 7 | 33.5 ± 1.3%§ | 10 | 22.5 ± 2.3% |

*NS. : $P < 10^{-3}$,
§$P = 0.11$.

What is claimed is:

1. A method of detecting the susceptibility of a patient to Alzheimer's disease, which comprises
    (a₁) determining the level of expression of the ε4 allele of the gene encoding apolipoprotein E in patients heterozygous, ε4/ε3 or ε4/ε2, for the apolipoprotein E genotype ε, wherein susceptibility to Alzheimer's disease is indicated by the presence of a mutation in the consensus sequence binding the Th1/E47cs transcription factor and an increase in the level of expression of the ε4 allele compared to a control population; or
    (a₂) determining the level of expression of the ε2 allele of the gene encoding apolipoprotein E in patients carrying the apolipoprotein E genotype ε2/ε3, wherein susceptibility to Alzheimer's disease is indicated by the presence of a mutation in the consensus sequence binding the Th1/E47cs transcription factor and a decrease in the level of expression of the ε2 allele compared to a control population.

2. The method according to claim 1, further comprising
    (b) identifying a G to T substitution within the consensus binding sequence TH1/E47cs at 186 bases from the first nucleotide of the TATA box of the gene encoding human apoE, wherein the presence of the mutation indicates a susceptibility to Alzheimer's disease.

3. The method according to claim 1, wherein a biological sample selected from the group consisting of cerebral tissue, lymphocytes, fibroblasts and other tissues capable of exhibiting a difference in expression of ε alleles of the apolipoprotein E gene is used to identify the mutation and to determine the levels of expression of the ε4 or ε2 allele with respect to the other allele.

4. A method of detecting the susceptibility of a patient to Alzheimer's disease independent of an ε polymorphism, which comprises identifying a mutation in the promoter region of the gene encoding apolipoprotein E in the consensus sequence binding the Th1/E47cs transcription factors; wherein the presence of the heterozygous mutation indicates a susceptibility to Alzheimer's disease.

5. The method according to claim 4, wherein the mutation exists in a region situated at 186 bases from the the first nucleotide TATA box of the gene encoding human apoe.

6. The method according to claim 4, wherein a biological sample selected from the group consisting of cerebral tissue, lymphocytes, fibroblasts and other tissues capable of exhibiting a difference in expression of ε alleles of the apolipoprotein E gene is used to identify the mutation.

* * * * *